(12) United States Patent
Miller

(10) Patent No.: US 7,029,922 B2
(45) Date of Patent: Apr. 18, 2006

(54) METHOD FOR RESUPPLYING REAGENTS IN AN AUTOMATIC CLINICAL ANALYZER

(75) Inventor: David Jeffrey Miller, Wilmington, DE (US)

(73) Assignee: Dade Behring Inc., Deerfield, IL (US)

( * ) Notice: Subject to any disclaimer, the term of this patent is extended or adjusted under 35 U.S.C. 154(b) by 117 days.

(21) Appl. No.: 10/623,309

(22) Filed: Jul. 18, 2003

(65) Prior Publication Data

US 2005/0014285 A1 Jan. 20, 2005

(51) Int. Cl.
- G01N 1/10 (2006.01)
- G01N 35/02 (2006.01)
- G05B 21/00 (2006.01)
- B01L 3/02 (2006.01)
- F01N 3/20 (2006.01)

(52) U.S. Cl. ............ 436/180; 422/100; 422/105; 422/106; 422/108; 422/62; 422/67; 422/68.1; 436/50; 436/55; 700/266; 700/281

(58) Field of Classification Search ......... 422/100, 422/105, 106, 108, 62–63, 67, 68.1; 436/174, 436/180, 50, 55; 700/266, 281
See application file for complete search history.

(56) References Cited

U.S. PATENT DOCUMENTS

| | | | |
|---|---|---|---|
| 4,188,190 A * | 2/1980 | Muraki et al. | 436/55 |
| 4,678,755 A | 7/1987 | Sinohara et al. | 436/43 |
| 4,910,691 A * | 3/1990 | Skeirik | 706/45 |
| 5,389,236 A * | 2/1995 | Bartholic et al. | 208/152 |
| 5,424,212 A | 6/1995 | Pinsl-Ober et al. | 436/50 |
| 5,550,053 A * | 8/1996 | Salpeter | 436/8 |
| 5,580,531 A * | 12/1996 | Vassiliou et al. | 422/108 |
| 5,597,733 A | 1/1997 | Beil et al. | 436/54 |
| 5,730,939 A | 3/1998 | Kurumada et al. | 422/67 |
| 5,741,708 A * | 4/1998 | Carey et al. | 436/49 |
| 5,885,530 A * | 3/1999 | Babson et al. | 422/65 |
| 5,902,549 A | 5/1999 | Mimura et al. | 422/65 |
| 6,022,746 A | 2/2000 | Fritchie et al. | 436/50 |
| 6,063,634 A * | 5/2000 | Chomka et al. | 436/54 |
| 6,080,364 A | 6/2000 | Mimura et al. | 422/67 |
| 6,127,184 A | 10/2000 | Wardlaw | 436/50 |
| 6,521,112 B1 * | 2/2003 | Balisky | 205/81 |
| 6,555,062 B1 * | 4/2003 | Lewis et al. | 422/63 |
| 6,579,713 B1 | 6/2003 | Olivier | 435/290.4 |
| 6,727,096 B1 * | 4/2004 | Wang et al. | 436/37 |
| 2001/0028864 A1 * | 10/2001 | Tyberg et al. | 422/100 |
| 2003/0175157 A1 * | 9/2003 | Micklash et al. | 422/70 |
| 2003/0202905 A1 * | 10/2003 | Devlin et al. | 422/64 |
| 2003/0229422 A1 * | 12/2003 | Martens et al. | 700/266 |
| 2004/0154965 A1 * | 8/2004 | Baum et al. | 210/85 |

* cited by examiner

Primary Examiner—Jill Warden
Assistant Examiner—Brian R. Gordon
(74) Attorney, Agent, or Firm—Leland K. Jordan

(57) ABSTRACT

A method for resupplying reagents inventoried on-board an automatic clinical analyzer by: comparing an averaged assay demand pattern on the analyzer for assays over a sequence of specifically defined time periods with the reagents inventoried on-board the analyzer to determine which reagents will be exhausted before the next following the sequence of specifically defined time periods, and, resupplying reagents appropriately.

6 Claims, 8 Drawing Sheets

METHOD FOR RESUPPLYING REAGENTS IN AN AUTOMATIC CLINICAL ANALYZER

FIELD OF THE INVENTION

The present invention relates to a method and apparatus for automatically processing a patient's biological fluids such as urine, blood serum, plasma, cerebrospinal fluid and the like. In particular, the present invention provides a method for resupplying chemical inventories in an automatic clinical analyzer.

BACKGROUND OF THE INVENTION

Various types of tests related to patient diagnosis and therapy can be performed by analysis of a sample of a patient's infection, bodily fluid or abscess for an analyte of interest. Patient samples are typically placed in closed sample tubes, the tubes transported to a clinical laboratory, placed into racks on an automated clinical analyzer and sample is extracted from the tubes. Subsequently, samples are combined in reaction vessels with various reagents extracted from reagent containers; the mixture is possibly incubated before being analyzed to aid in treatment of the patient. Interrogating measurements, turbidimetric or fluorometric or the like, are made to ascertain end-point or reaction rate values from which the amount of analyte in the sample may be determined, using well-known calibration techniques.

Automated clinical analyzers improve operating efficiency by providing results more rapidly while minimizing operator or technician error. Due to increasing demands on clinical laboratories regarding assay throughput, the efficiency of handling patient samples and reagents within an analyzer continually needs to be increased, and an important factor is the ability to maintain an adequate Inventory of reagents, quality control, and calibration solutions on-board and readily available such analyzers. Hereinafter, reagents, quality control, and calibration solutions may be referred to as standard chemical solutions.

The sample rack is usually placed by an operator in an input portion of the analyzer and automatically moved by the analyzer to an aliquotting location where an aliquot of the liquid patient sample is extracted, usually by aspiration using a hollow probe from the sample container. Aliquot samples from a number of different patient samples may be dispensed into a plurality of interim vessels or wells formed as an integral array of small open cup-like vessels, herein called an aliquot vessel array, like that described in U.S. patent Ser. No. 10/037,512, assigned to the assignee of the present invention. Aliquot vessel arrays are transported to a sampling location where an appropriate amount of the aliquot sample is extracted by a sampling probe and dispensed by a sampling probe into a reaction cuvette. In addition, standard chemical solutions required to conduct specified assays are extracted at a reagenting location from appropriate assay chemical containers or containers using hollow probes that are subsequently shuttled to assay chemical solution dispensing locations where standard chemical solutions are dispensed into the reaction cuvette.

SUMMARY OF THE INVENTION

The present invention provides a method to automatically resupply standard chemical solutions reagent containers and calibration solution vials on a clinical analyzer by analyzing the demand pattern historically placed upon the analyzer for the different assays the analyzer is equipped to perform. At a user selected time period before the standard chemical solutions in all standard chemical solutions containers within the analyzer's reagent servers are expected to be exhausted, based on a comparison of historical day specifically defined consumption with the inventory of standard chemical solutions already available, an alert message is provided so that appropriate measures may be undertaken by an operator to ensure an uninterrupted, timely supply of standard chemical solutions within the analyzer.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
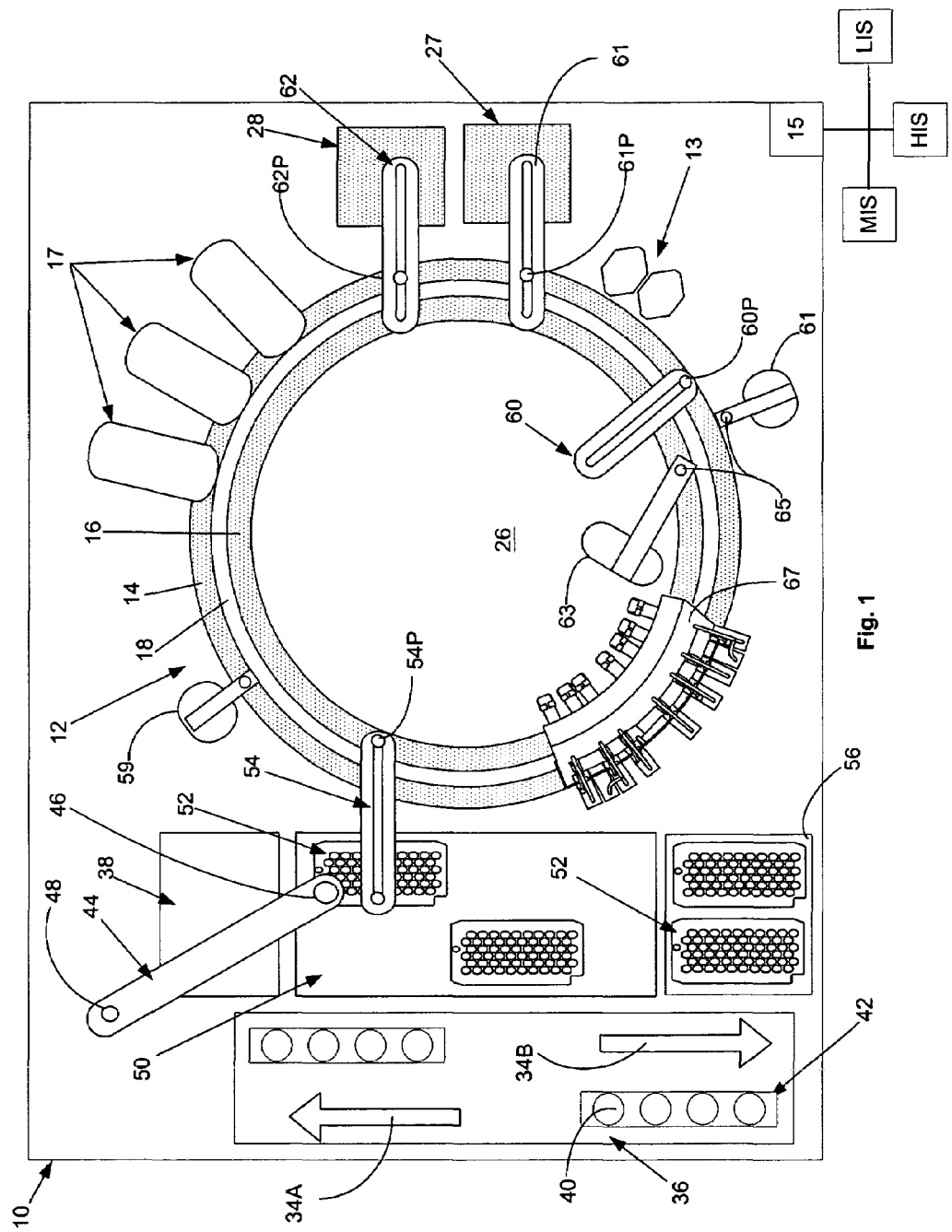
FIG. 1 is a schematic plan view of an automated analyzer in which the present invention may be employed to advantage.
Figure 2:
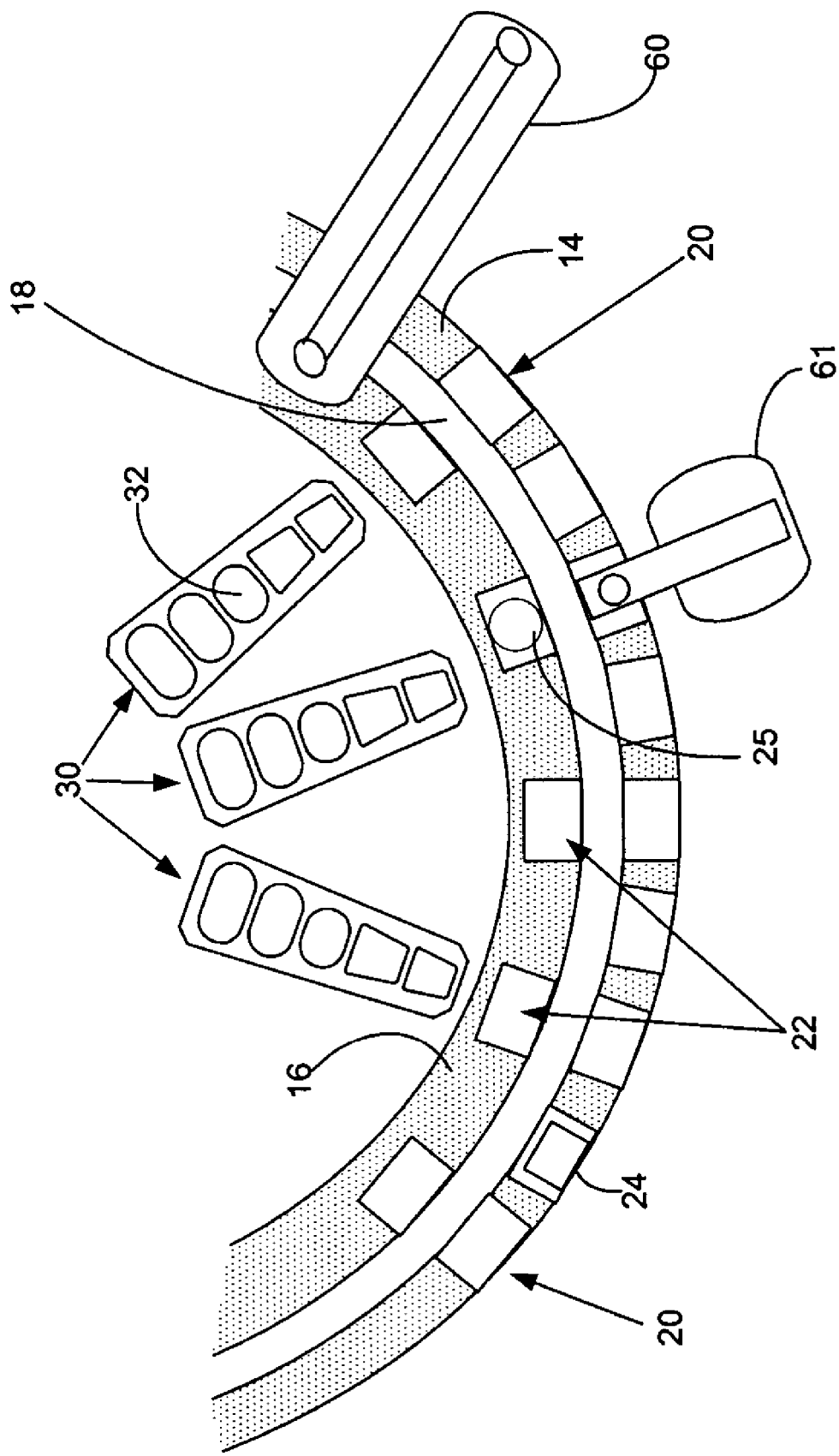
FIG. 2 is an enlarged schematic plan view of a portion of the analyzer of FIG. 1.

FIG. 1, taken with FIG. 2, shows schematically the elements of an automatic chemical analyzer 10 in which the present invention may be advantageously practiced, analyzer 10 comprising a reaction carousel 12 supporting an outer cuvette carousel 14 having cuvette ports 20 formed therein and an inner cuvette carousel 16 having vessel ports 22 formed therein, the outer cuvette carousel 14 and inner cuvette carousel 16 being separated by a open groove 18. Cuvette ports 20 are adapted to receive a plurality of reaction cuvettes 24 like disclosed in co-pending application Ser. No. 09/949,132 assigned to the assignee of the present invention and containing various reagents and sample liquids for conventional clinical and immunoassay assays while vessel ports 22 are adapted to receive a plurality of reaction vessels 25 that contain specialized reagents for ultra-high sensitivity luminescent immunoassays. Reaction carousel 12 is rotatable using stepwise movements in a constant direction, the stepwise movements being separated by a constant dwell time during which carousel 12 is maintained stationary and computer controlled assay operational devices 13, such as sensors, reagent add stations, mixing stations and the like, operate as needed on an assay mixture contained within cuvettes 24 and reaction vessels 25.

Analyzer 10 is controlled by software executed by the computer 15 based on computer programs written in a machine language like that used on the Dimension® clinical chemistry analyzer sold by Dade Behring Inc, of Deerfield, Ill., and widely used by those skilled in the art of computer-based electromechanical control programming. Computer 15 also executes application software programs for performing assays conducted by various analyzing means 17 within analyzer 10. Computer 15 is interlinked using known interface software applications with a Laboratory Information System (LIS) and/or a Hospital Information System (HIS) so that information concerning patients, patient assay requests, assay results, analyzer status, and the like, may be immediately accessible as needed by laboratory personnel.

Figure 3A:
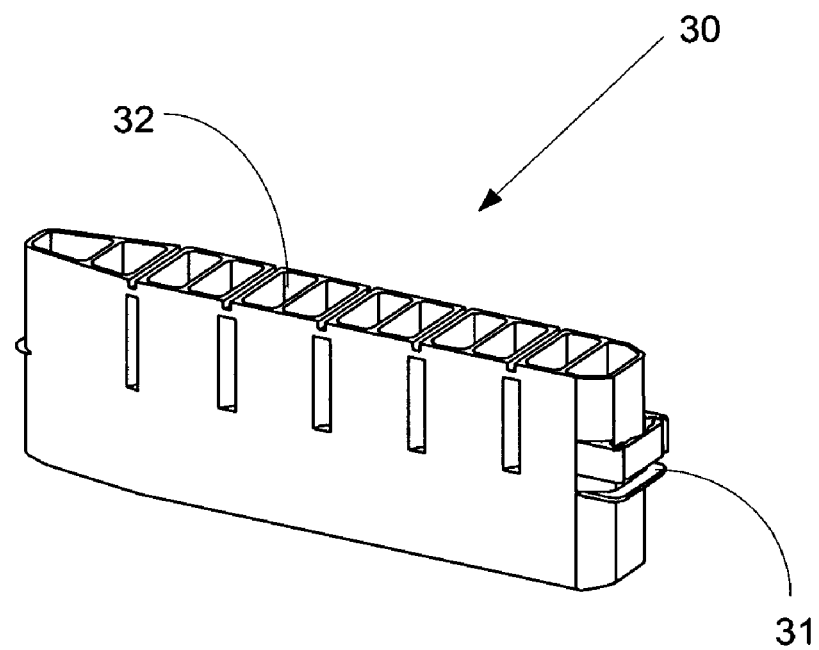
FIG. 3A is a perspective view of a reagent container useful in the analyzer of FIG. 1 and useful in performing the present invention.
Figure 3B:
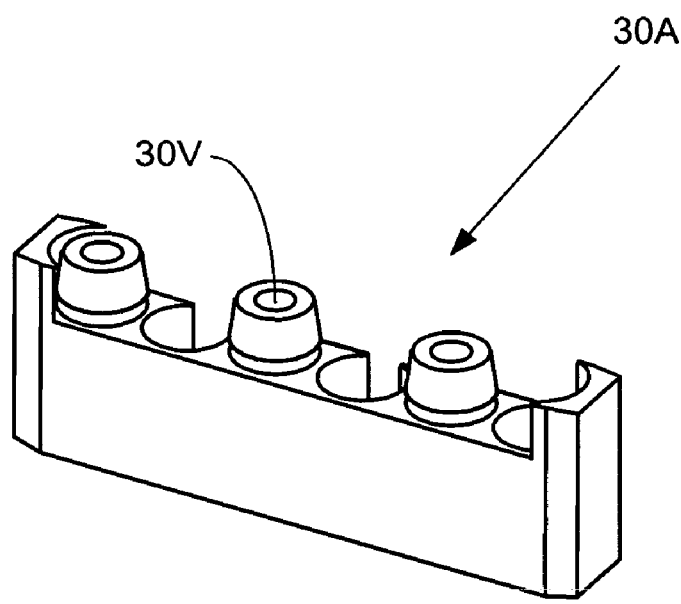
FIG. 3B is a perspective view of a calibration solution vial container useful in the analyzer of FIG. 1 and useful in performing the present invention.

Temperature-controlled reagent storage areas 26, 27 and 28 store a plurality of multi-compartment elongate reagent containers 30 like that illustrated in FIG. 3A and containing reagents necessary to perform a given assay within a number of wells 32, each well containing as much as 3.4 mL of a given reagent. Container 30 has features to enable analyzer 10 to automatically determine whether a reagent container 30 is new and unused or whether the reagent container 30 has been previously used and possibly become contaminated whenever a reagent container 30 is initially placed onto an analyzer. FIG. 3B shows a calibration vial container 30A containing calibration solutions of known analyte concentrations in calibration solution vials 30V, the solutions being to conduct well-know calibration and quality control procedures within analyzer 10. Calibration vial containers 30A are also inventoried upon analyzer 10 within reagent storage areas 26, 27 and 28

A bi-directional incoming and outgoing sample tube transport system 36 having input lane 34A and output lane 34B transports incoming individual sample tubes 40 containing liquid specimens to be tested and mounted in sample tube racks 42 into the sampling arc of a liquid sampling arm 44. Liquid specimens contained in sample tubes 40 are identified by reading bar coded indicia placed thereon using a conventional bar code reader to determine, among other items, a patient's identity, the tests to be performed, if a sample aliquot is to be retained within analyzer 10 and if so, for what period of time. It is also common practice to place bar coded indicia on sample tube racks 42 and employ a large number of bar code readers installed throughout analyzer 10 to ascertain, control and track the location of sample tubes 40 and sample tube racks 42.

Figure 4:
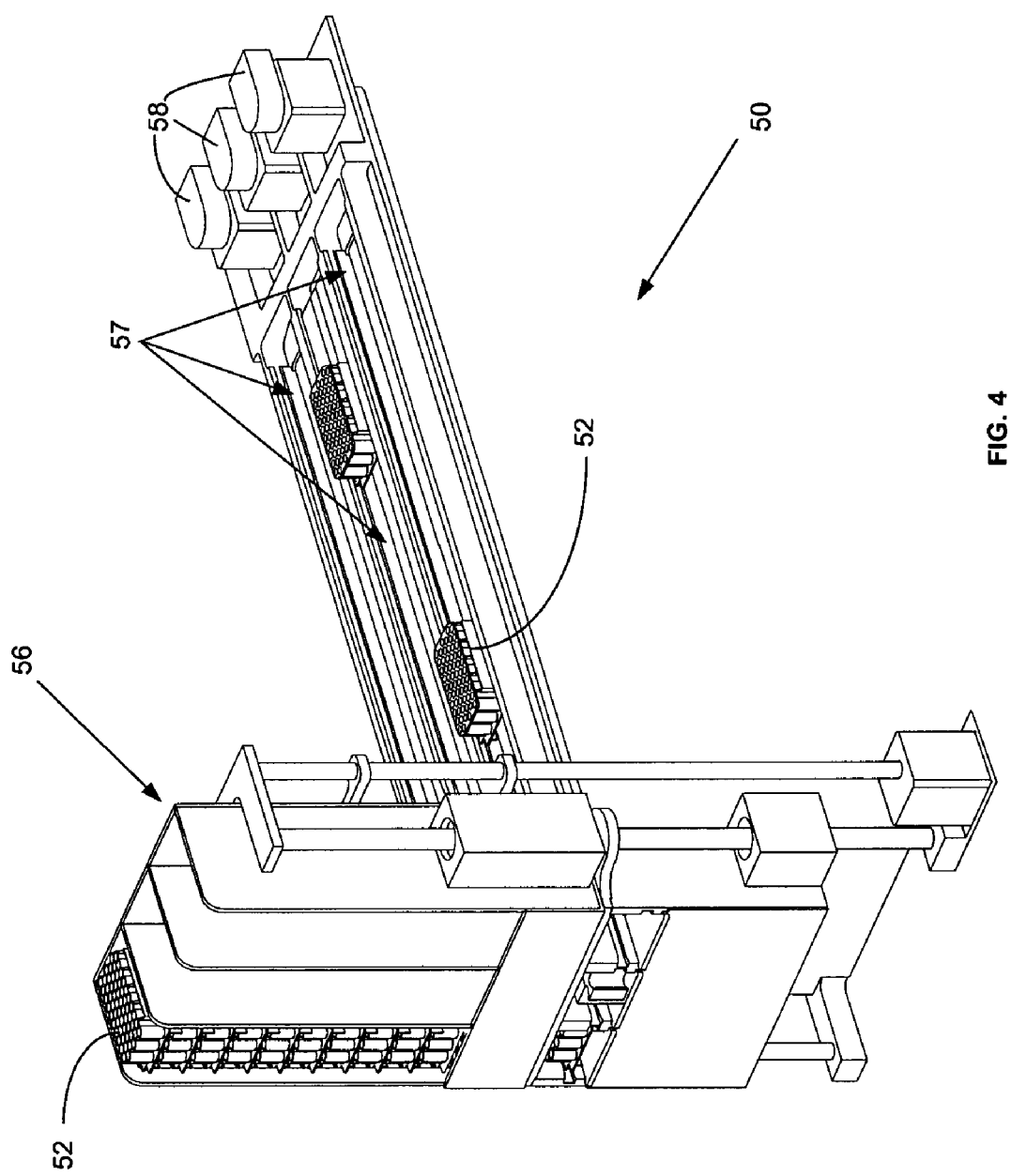
FIG. 4 is a perspective view of an aliquot vessel array storage and handling unit useful in the analyzer of FIG. 1.
Figure 5:
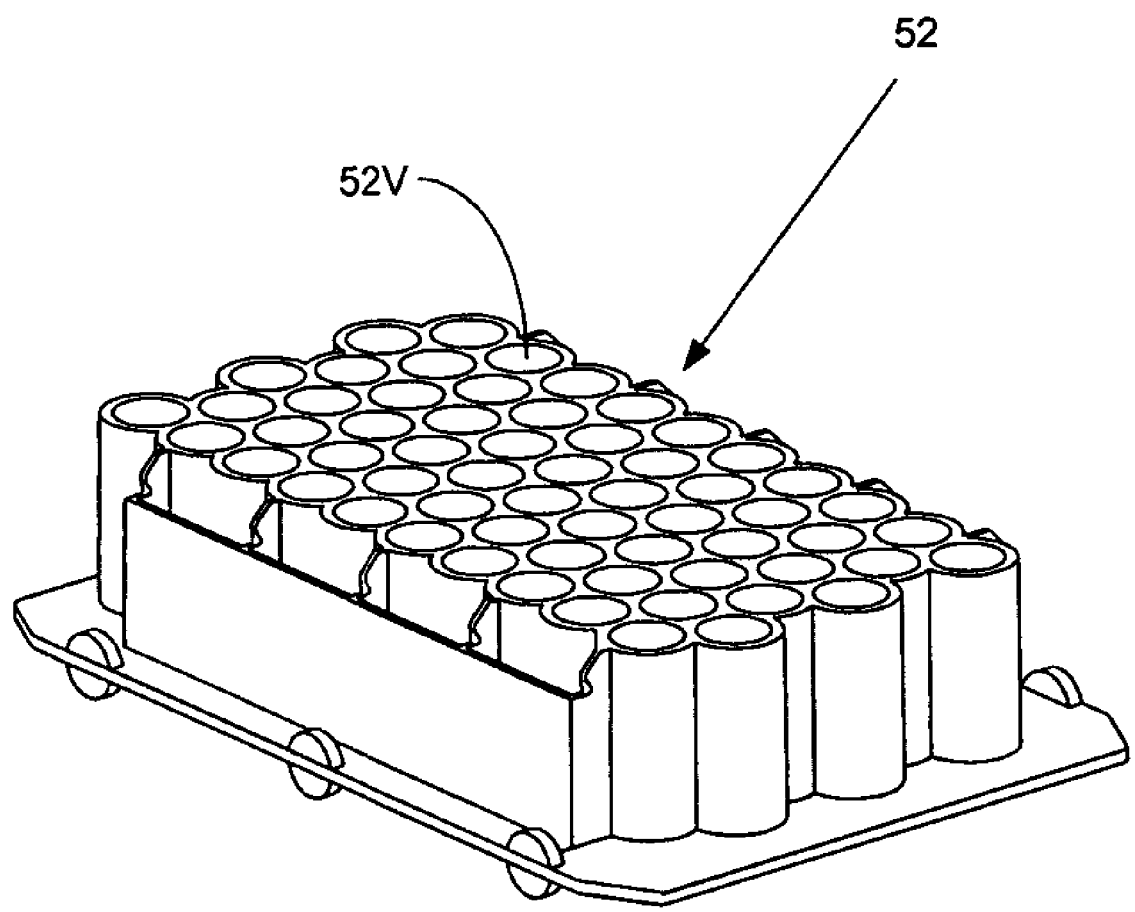
FIG. 5 is a perspective elevation view of an aliquot vessel array useful in the analyzer of FIG. 1.

Sampling arm 44 supports a liquid sampling probe 46 mounted to a rotatable shaft 48 so that movement of sampling arm 44 describes an arc intersecting the sample tube transport system 36 and an aliquot vessel array transport system 50, as seen in FIG. 4. Sampling arm 44 is operable to aspirate liquid sample from sample tubes 40 and to dispense an aliquot sample into one or more of a plurality of vessels 52V in aliquot vessel array 52, as seen in FIG. 5, depending on the quantity of sample required to perform the requisite assays and to provide for a sample aliquot to be retained by analyzer 10 within environmental chamber 38.

Aliquot vessel array transport system 50 comprises an aliquot vessel array storage and dispense module 56 and a number of linear drive motors 58 adapted to bi-directionally translate aliquot vessel arrays 52 within a number of aliquot vessel array tracks 57 below a sample aspiration and dispense arm 54 located proximate reaction carousel 12. Sample aspiration and dispense arm 54 is controlled by computer 15 and is adapted to aspirate a controlled amount of sample from individual vessels 52V positioned at a sampling location within a track 57 using a conventional liquid probe 54P and then liquid probe 54P is shuttled to a dispensing location where an appropriate amount of aspirated sample is dispensed into one or more cuvettes 24 in cuvette ports 20 for testing by analyzer 10 for one or more analytes. After sample has been dispensed into reaction cuvettes 24, conventional transfer means move aliquot vessel arrays 52 as required between aliquot vessel array transport system 50, environmental chamber 38 and a disposal area, not shown.

A number of reagent aspiration and dispense arms 60, 61 and 62 each comprising at least one conventional liquid reagent probe, 60P, 61P and 62P, respectively, are independently mounted and translatable between reagent storage areas 26, 27 and 28, respectively. Probes 60P, 61P and 62P are conventional mechanisms for aspirating reagents required to conduct specified assays at a reagenting location from wells 32 in an appropriate reagent container 30, the probes 60P, 61P and 62P subsequently being shuttled to a reagent dispensing location where reagent(s) are dispensed into reaction cuvettes 24. Probes 60P, 61P and 62P are also used for aspirating calibration and control solutions from calibration solution vials 30V as required to conduct calibration and control procedures to ensure proper operation of analyzer 10, the probes 60P, 61P and 62P subsequently being shuttled to a calibration solution dispensing location where solutions(s) are dispensed into reaction cuvettes 24 and analyzed by analyzing means 17.

Reaction cuvette load station 61 and reaction vessel load station 63 are respectively positioned proximate outer cuvette carousel 14 and inner vessel carousel 16 and are adapted to load reaction cuvettes 24 into cuvette ports 20 sideways as described later and reaction vessels 25 into vessel ports 22 using for example a translatable robotic arm 65. In operation, used cuvettes 24 in which an assay has been finally conducted, are washed and dried in a wash station 67 like disclosed in co-pending application Ser. No. 10/623,360 assigned to the assignee of the present invention. Subsequent assays are conducted in cleaned used cuvettes 24 unless dictated otherwise for reasons like disclosed in co-pending application Ser. No. 10/318,804 assigned to the assignee of the present invention. Cuvette unload station 59 is adapted to remove unusable reaction cuvettes 24 from cuvette ports 20 again using a translatable robotic arm 65 like seen on load stations 61 and 63.

Figure 6:
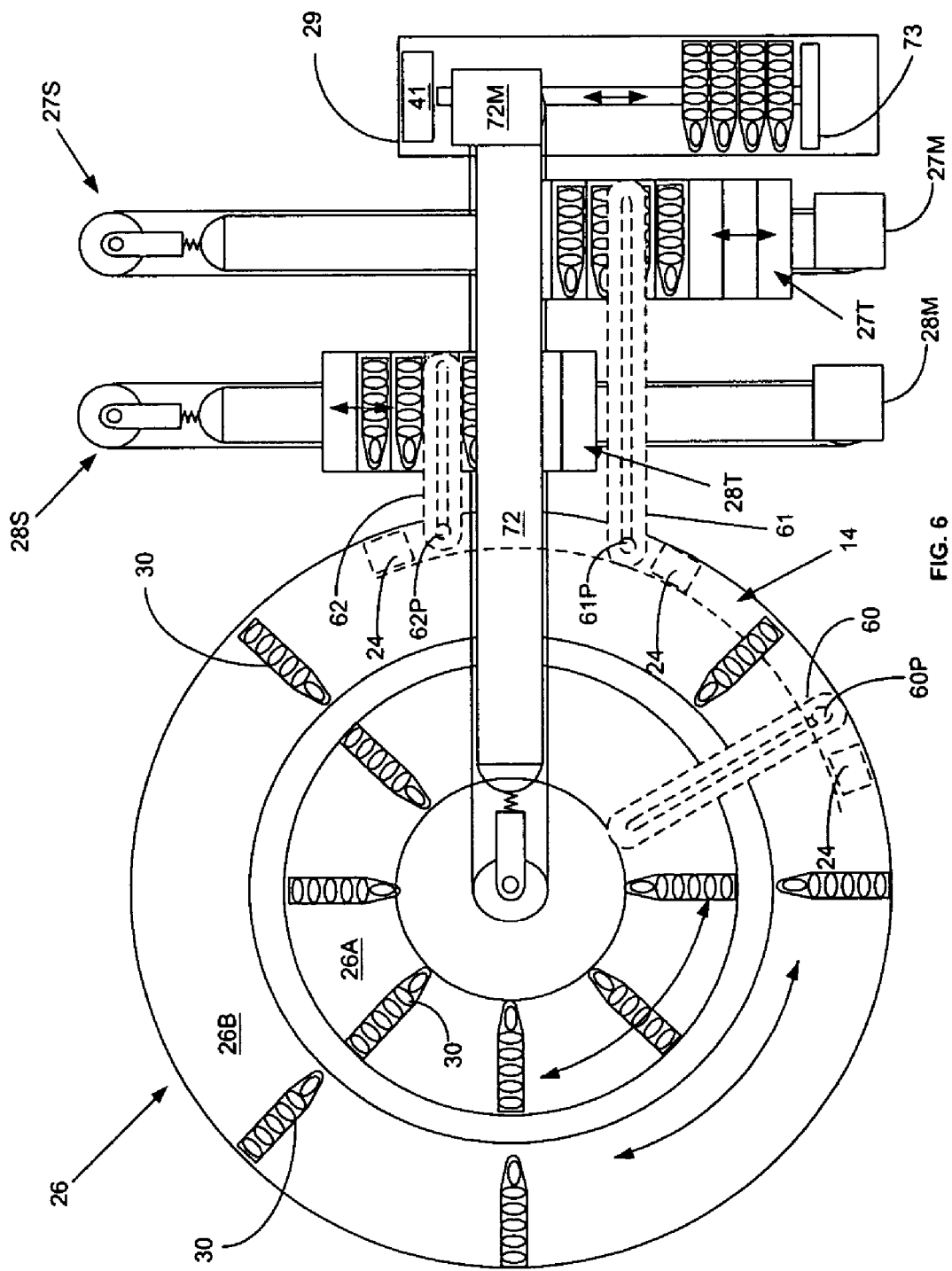
FIG. 6 is a schematic plan view of a container transport system useful in the analyzer of FIG. 1 and in performing the present invention; and, FIG. 7 is a perspective view of a container shuttle useful in the analyzer of FIG. 1 and in performing the present invention; and, FIG. 8 is a perspective view of a container tray shuttle useful in the analyzer of FIG. 1 and in performing the present invention.

In order to implement the present method for resupplying assay reagents and calibration solutions, analyzer 10 includes a single, bi-directional linear container shuttle 72 illustrated in FIG. 6 and adapted to remove reagent containers 30 and calibration vial containers 30A from a container loading tray 29 having a motorized rake 73 that automatically locates containers 30 and 30A at a loading position beneath container shuttle 72. Shuttle 72 is further adapted to dispose a reagent container 30 or a calibration vial container 30A into slots in at least one slotted reagent container tray 27T or 28T within reagent storage areas 27 or 28, respectively. In a similar fashion, shuttle 72 is even further adapted to remove reagent containers 30 or calibration vial containers 30A from reagent container trays 27T and 28T and to dispose such reagent containers 30 or calibration vial containers 30A into either of two concentric reagent carousels 26A and 26B within reagent storage area 26. Shuttle 72 is also adapted to move reagent containers 30 and calibration vial containers 30A between the two concentric reagent carousels 26A and 26B. As indicated by the double-headed arc-shaped arrows, reagent carousel 26A may be rotated in both directions so as to place any particular one of the reagent containers 30 or calibration vial containers 30A disposed thereon beneath reagent aspiration arm 60. Although reagent carousel 26B may also contain reagent containers 30 and calibration vial containers 30A accessible by reagent aspiration arms 60 and 62, carousel 26B is preferably designated only for storing excess inventory of reagent containers 30 and calibration vial containers 30A. Any one of the reagent containers 30 disposed in reagent container trays 27T and 28T may be located at a loading position beneath container shuttle 72 or at a reagent aspiration location beneath aspiration and dispensing arms 61 and 62, respectively, by reagent container shuttles 27S and 28S within reagent storage areas 27 and 28, respectively. Reagent aspiration arms 60 and 62 are shown in dashed lines to indicate that they are positioned above the surfaces of reagent containers 30 inventoried in carousel 26B, and reagent container trays 27T and 28T, respectively. Reaction cuvettes 24 supported in outer cuvette carousel 14 are also both shown in dashed lines to indicate that they are positioned above the surfaces of reagent containers 30. A container shuttle system like seen in FIG. 6, is described in co-pending U.S. patent Ser. No. 10/623,310, assigned to the assignee of the present invention.

Figure 7:
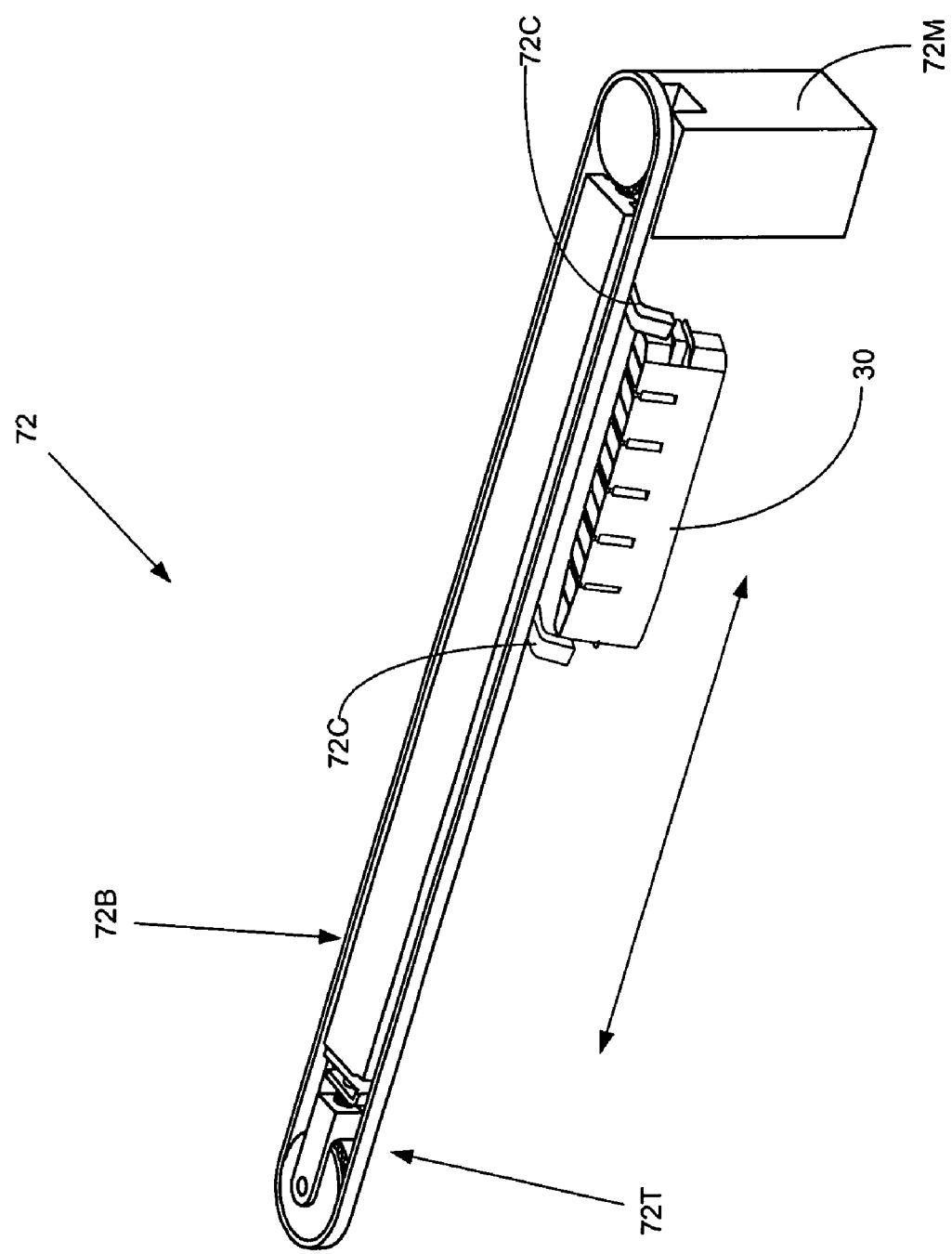
Figure 8:
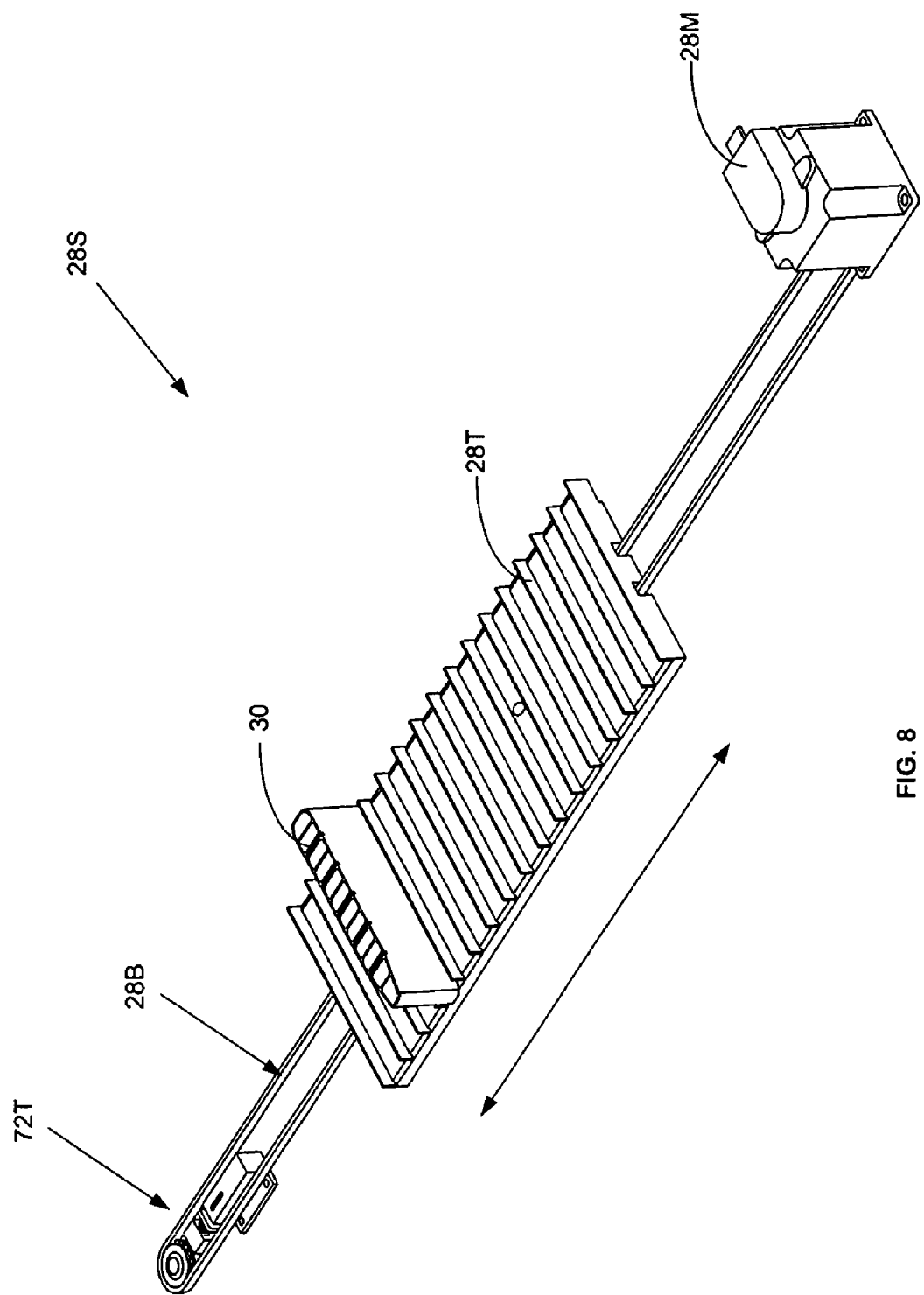

Container shuttle seen in FIG. 7 is adapted to automatically compensate for unknown changes in length of a drivebelt 72B driven by motor 72M by an automated tensioner 72T, disclosed in co-pending application Ser. No. 10/623,311 and assigned to the assignee of the present invention, and adapted to maintain a constant tension on the drivebelt 72B regardless of rapid changes in its driving direction so that reagent containers 30 and calibration vial containers 30A attached thereto by clamps 72C may be accurately positioned along the direction of drivebelt 72B, as indicated by the double-ended arrow, and disposed at their intended location beneath reagent container shuttle 72 or within storage areas 26, 27 or 28 as drivebelt 72B wears. Reagent container shuttles 27S and 28S are similar in design to one another, and as seen in FIG. 8, include a reagent container tray 28T secured to one leg of a drivebelt 28B so that tray 28T is free to be driven to and from along the direction of drivebelt 28B, as indicated by the double-ended arrow. Consequently, reagent containers 30 within slots in tray 28T may be automatically positioned at a pick-up location beneath container shuttle 72.

From the preceding description of analyzer 10, it is clear to one skilled in the art that the capabilities of analyzer 10 under the control of computer 15 include the ability to automatically to move reagent containers 30 and calibration vial containers 30A between container loading tray 29, reagent container trays 27T and 28T, and reagent carousels 26A and 26B. By means of shuttles 27S and 28S, analyzer 10 is further capable of moving reagent containers 30 and calibration vial containers in reagent container trays 27T and 28T to appropriate aspiration locations by probes 61P and 62P, respectively, (or to a loading location beneath shuttle 72) so that in combination with the capability of reagent carousels 26A and 26B to place any reagent container 30 or calibration vial container 30A beneath reagent aspiration arms 60P, 61P and 62P. Analyzer 10 thus includes an automated random access reagent and calibration solution resupply system with the flexibility to position a large number of different reagents and calibration solutions at different aspiration locations.

A key factor in maintaining an optimum assay throughput within analyzer 10 is the ability to timely resupply reagent containers 30 into reagent storage areas 26, 27 and 28 before the reagents contained therein become exhausted. Similarly important is the ability to timely resupply calibration and Quality Control solutions in vial containers 30A before the solutions contained therein become exhausted so that calibration and control procedures may be conducted as required, whether this be based on the basis of time between calibrations or number of assays performed since an immediately previous calibration or number of assay results outside normal ranges, or changes in the performance of the analyzer. This challenge may be met by timely equipping analyzer 10 with additional requisite calibration and Quality Control solutions used in calibration and control procedures and called standard chemical solutions herein for convenience, before they become exhausted, thereby maintaining assay throughput of analyzer 10 uninterrupted.

In order to maintain continuity of assay throughput, and as taught by the present invention, computer 15 is programmed to track reagent and assay chemical solution consumption along with time, and date of consumption of all reagents consumed out of each reagent container 30 and assay chemical solutions consumed out of each vial container 30A on a per reagent container, per calibration vial container, per Quality Control container, per assay, and per calibration basis, for specifically defined time periods. Using this consumption data, time, and current reagent container 30 and calibration vial container 30A inventory data of already on-board standard chemical solutions within storage areas 26, 27 and 28, computer 15 is programmed to make an inventory demand analysis for specifically defined time periods so as to determine future assay inventory demands for the specifically defined time periods and display or issue to an operator a list of all of the reagent containers 30 and calibration/Quality Control vial containers 30A that will be needed in the future in a timely manner prior to the actual need of said reagent container 30 and calibration/Quality Control vial containers 30A. In some instances, reagents in reagent container 30 must be hydrated or diluted prior to use and such a time factor must also be included in the inventory demand analysis. Addition of said reagent containers 30 and calibration/Quality Control vial containers 30A by an operator insures sufficient reagent and calibration solution supply to meet future needs of analyzer 10.

It should be appreciated by the reader that making an inventory demand analysis for specifically defined time periods, as opposed to using an inventory demand analysis averaged over specifically defined time periods, is a key factor in practicing the present invention. What has been discovered is that the assay demand load pattern, for example on a Monday, may be very different from the assay demand load pattern, for example on a Thursday. Further, it has been discovered that the assay demand load pattern, for example on a given Tuesday, is most likely going to be very similar to the demand load pattern on the previous several Tuesdays. The basis for a specifically defined time period assay demand load analysis is due to several factors among which are a range of social practices, for example, sporting events typically being on weekends and/or increased social events at holidays and the like. In addition, for reasons of efficiency, some clinical laboratories schedule select assays, for example, PSA tests, on a certain day near middle of the week, and some out-patient tests, for example glucose, are scheduled earlier in the week. Finally, certain surgeons schedule select types of surgery early In the week and other types of surgery near the end of the week, resulting in different daily patterns of pre-operation patient assays. Further contributing to the assay demand load pattern is the fact that different laboratories have different assay demand patterns, depending, for example, upon whether the laboratory serves an urban community where trauma is more likely than in a rural community, upon whether the laboratory serves a medical research university, upon whether the laboratory serves a specialized hospital like a pediatric hospital, and the like.

On a regular basis, for example daily, as taught by the present invention, the chemical solution consumption data is also transmitted to an external computer system located within an LIS or HIS or to a Manufacturer Information System (MIS) remotely at the manufacturer of reagent containers 30 and calibration/Quality Control vials 30A. The external computer systems use the consumption data to determine the need for re-order of reagent containers 30 and vial containers 30A in a timely manner so as to ensure that the reagents in reagent containers 30 and standard chemical solutions in vial containers 30A are available in local inventory for future use. In a preferred embodiment of the current invention, the reagent container 30 and vial container 30A consumption data are used by the manufacturer of reagent containers 30 and calibration vial containers 30A and compared to the manufacture's shipment data to determine re-order quantities. The manufacturer automatically ships additional reagent containers 30 and calibration vial containers 30A to the location of analyzer 10 as needed to ensure a continuous supply at that location.

In the instance of analyzer 10 installed in a hospital specializing in female patients, the first 8 assays listed in the second column of Table 1 are requested generally twice as often than the remaining 16 assays. The demand for these assays generally varies between 40–80% in hospitals in the United States and in certain instances 100% of the demand load in some European countries. In contrast, the demand for the remaining 16 assays generally varies between 5–30% in hospitals in both the United States and some European countries. Because the population served by a hospital and a laboratory and because the activities of that population and the environment of that population generally remain constant or very slowly changing on a specifically defined time period basis, a fairly accurate historical pattern of future assay demand for that specifically defined time period can be complied. Given the assay demand for that specifically defined time period and data concerning the number of assays that can be routinely conducted using a typical reagent container 30, as indicated in column one of Table 1, computer 15 is programmed to display or issue a message to an operator identifying the reagent containers 30 and vial containers 30A that will be required to be placed into container loading tray 29, for example 12 hours later, in order that reagent container 30 and vial containers 30A required to maintain an uninterrupted throughput of all assays on analyzer 10 are in fact timely available within one of the reagent storage areas 26, 27 or 28.

TABLE 1

| Assays Per Reagent Container 30 | Assay Type |
| --- | --- |
| 540 | 1. Total CO2 |
| 450 | 2. Creatinine |
| 480 | 3. Blood Urea Nitrogen |
| 300 | 4. Calcium |
| 600 | 5. Glucose |
| 400 | 6. Alkaline Phosphatase |
| 360 | 7. Albumin |
| 240 | 8. Cholesterol |
| 240 | 9. Creatine Kinase |

TABLE 1-continued

| Assays Per Reagent Container 30 | Assay Type |
| --- | --- |
| 210 | 10. Gamma Glutamyl Transferase |
| 150 | 11. Iron |
| 100 | 12. HDL Chol |
| 180 | 13. Amylase |
| 45 | 14. MMB |
| 40 | 15. Digoxin |
| 40 | 16. Phenytoin |
| 100 | 17. T Uptake |
| 30 | 18. Myoglobin |
| 40 | 19. Acetaminophen |
| 80 | 20. Free T4 |
| 40 | 21. Ferritin |
| 40 | 22. Lactic Acid |
| 60 | 23. Lithium |
| 40 | 24. T3 |
| 60 | 25. Free T3 |
| 40 | 26. Digitoxin |

In an exemplary embodiment of the present invention, the specifically defined time periods are 24-hour periods of time corresponding to the 7 days in a week. Conventionally, these will be called Monday, Tuesday, etc. According to the present invention, for example on a Monday, computer 15 will look up from within the historical records of assays maintained in memory storage by computer 15, the assay demand pattern for the previous 4 Tuesdays, mathematically average the assay demand pattern for those previous 4 Tuesdays to produce an average assay demand for Tuesday for all assays analyzer 10 is equipped to perform, and add 3 Standard Deviations for each individual assay, based on the mathematical averaging analysis. The resulting assay demand pattern is the anticipated Tuesday assay demand pattern forecast to occur on Tuesday and will also include demand for calibration and Quality Control solutions. Computer 15 is further programmed to examine the on-board inventory of reagents in reagent containers 30 and calibration and Quality Control solutions in vials 30V already existing within storage areas 26, 27 and 28 on Monday. Next, computer 15 is programmed to determine the difference between the anticipated Tuesday assay demand pattern and the Monday on-board inventory of reagents and calibration and Quality Control solutions in order to identify those reagent containers 30 and vial containers 30A that need to be placed by an operator into tray 29 on Tuesday so that analyzer 10 will be equipped with a full inventory of reagents and calibration and Quality Control solutions with which to conduct the Tuesday assay demand pattern. Finally, computer 15 is programmed to display on Monday a message to an operator identifying those reagent containers 30 and vial containers 30A that need to be placed by an operator into tray 29 on Tuesday. On Tuesday, the operator obtains those reagent containers 30 and vial containers 30A that need to be placed into tray 29 from a conventional storage unit and places them into tray 29. Typically, the analysis described above may be conducted near the end of a working day, or at the end of a particular work shift, so as to use the most accurate possible information as to the inventory levels of reagents and calibration and Quality Control solutions, and so that sufficient time will be available to allow an operator to obtain the reagent containers 30 and vial containers 30A that need to be placed into container loading tray 29 the following morning., or at the beginning of a particular work shift.

A very simplified illustration of the present invention may be found in Table 2, wherein an average assay demand is conducted on Monday, using the most recent historical Tuesday assay demand for the four previous Tuesdays, for Total CO2, Creatinine, and BUN is 1255, 1140, and 1050, respectively. In view of the number of assays that may be conducted in single different reagent containers 30 containing the reagents needed to perform Total CO2, Creatinine, and BUN assays, and considering the on-board inventory of the different reagent containers 30 as indicated, it is clear that 1 additional reagent container 30 for Total CO2 is needed for Tuesday and that 2 additional reagent containers 30 for Creatinine and BUN is needed for Tuesday. This information is provided as described above so that the requisite different reagent containers 30 may be timely supplied into tray 29 of analyzer and shuttled throughout analyzer 10 as required by shuttle system like seen in FIG. 6 in order to maintain a continuous throughput within analyzer 10.

TABLE 2

| Assays Per Reagent Container 30 | Assay Type | Averaged Assay Demand | Reagent Containers 30 on Analyzer 10 | Additional Reagent Containers 30 Needed on Analyzer 10 |
| --- | --- | --- | --- | --- |
| 540 | Total CO2 | 1255 | 2 | 1 |
| 450 | Creatinine | 1140 | 1 | 2 |
| 480 | BUN | 1050 | 1 | 2 |

This embodiment of the present method for resupplying reagents and calibration and Quality Control solutions is then repeated on Tuesday mathematically average the assay demand pattern for those previous 4 Wednesdays to produce an average assay demand for Wednesdays for all assays analyzer 10 is equipped to perform, so that analyzer 10 may be equipped by means of the present invention with a full inventory of reagents and calibration and Quality Control solutions with which to conduct the Wednesday assay demand pattern. This specifically defined time period assay demand analysis and resuppy method is continuously conducted daily throughout the week and then repeated on a weekly basis.

It will be appreciated by those skilled in that art that a number of variations may be made in the above described method and still achieve the essence of the present invention. Different specifically defined time periods may be defined, or a different number of previous but the same specifically defined time periods may be used to calculate an average assay demand for that specifically defined time period, and other variations may be employed and still be within the method disclosed For these reasons, the present invention is not limited to those embodiments precisely shown and described in the specification but only by the following claims.

I claim:

1. A method for resupplying reagents inventoried on-board an automatic clinical analyzer by:
averaging the assay demand pattern placed upon the analyzer for assays conducted on a specific day of a week over plurality of weekly time periods; following the plurality of weekly time periods, inventorying the reagents on board said analyzer, comparing the averaged assay demand pattern for said specific day of the week with the reagents inventoried on-board the analyzer, thereby determining which reagents are forecast to be exhausted before the arrival of said specific day of the week in an immediate week following said plurality of weeks and,
resupplying reagents to ensure an uninterrupted supply of reagents within the analyzer for said specified day during said immediate week.

2. The method of claim 1 wherein resupplying the reagents includes displaying or issuing an alert message to an operator identifying the type of and number of reagents forecast to be exhausted and that need to be resupplied.

3. The method of claim 1 wherein resupplying the reagents includes displaying or issuing an alert message to an LIS or HIS where the analyzer is located identifying the type of and number of reagents forecast to be exhausted and that need to be resupplied.

4. The method of claim 1 wherein resupplying the reagents includes measures include displaying or issuing an alert message to an MIS identifying the type of and number of reagents forecast to be exhausted and that need to be resupplied.

5. A method for resupplying standard chemical solutions inventoried on-board an automatic clinical analyzer by:
averaging a daily calibration and control procedure demand pattern placed upon the analyzer for calibration and control procedures during a specific day of a week over a plurality of weekly time periods; following the plurality of weekly time periods, inventorying standard solutions on board said analyzer and determining a calibration and control procedure for said inventoried solutions,
prior to any specific one of the seven twenty-four hour daily periods subsequent to the seven twenty-four hour daily time periods, compare comparing the averaged calibration and control procedure demand pattern for that said specific day of the week one of the seven twenty-four hour daily periods with the standard chemical solutions inventoried on-board the analyzer, thereby determining which standard chemical solutions are forecast to be exhausted before the arrival of said specific day of the week in an immediate week following said plurality of weeks and, resupplying reagents to ensure an uninterrupted supply of reagents within the analyzer for said specified day during said immediate week.

6. A method for resupplying reagents inventoried on-board an automatic clinical analyzer by: averaging a daily assay demand pattern placed upon the analyzer for assays conducted on a specific day of a week over a plurality of weekly time periods; following the plurality of weekly time periods, inventorying the reagents on board said analyzer, comparing the averaged assay demand pattern for said specific day of the week with the reagents inventoried on-board the analyzer, thereby determining which reagents are forecast to be exhausted before the arrival of said specific day of the week in an immediate week following said plurality of weeks resupplying reagents to ensure an uninterrupted supply of reagents within the analyzer for said specified day during said immediate week, wherein averaging the assay pattern includes tracking reagent and calibration solution consumption along with time and date of consumption of all reagents consumed on a per reagent container, per calibration vial container, per assay, and per calibration basis.

* * * * *

UNITED STATES PATENT AND TRADEMARK OFFICE
CERTIFICATE OF CORRECTION

PATENT NO. : 7,029,922 B2 Page 1 of 1
APPLICATION NO. : 10/623309
DATED : April 18, 2006
INVENTOR(S) : David Jeffrey Miller It is certified that error appears in the above-identified patent and that said Letters Patent is hereby corrected as shown below:

Column 9, in Claim 1, line 60 between the words "averaging" and "assay"; please delete the "the" word and insert -- a daily --.

Signed and Sealed this

Tenth Day of June, 2008

JON W. DUDAS
*Director of the United States Patent and Trademark Office*